Figure 1:
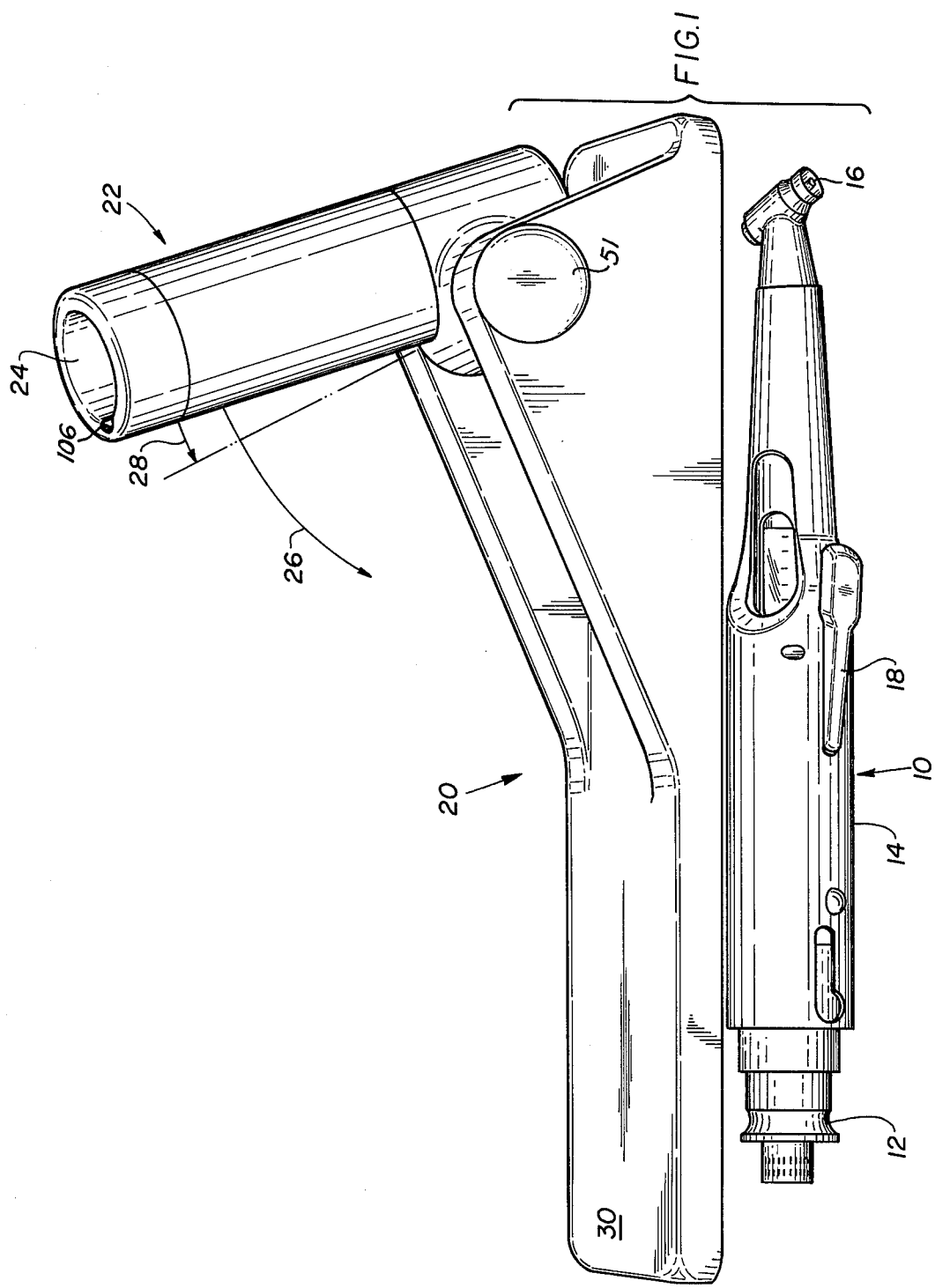

United States Patent [19]
Doherty et al.

[11] 4,090,512
[45] May 23, 1978

[54] DEVICE FOR SPRING-LOADING A NEEDLELESS INNOCULATOR

[76] Inventors: Norman R. Doherty, 870 Main St., Farmingdale, N.Y. 11735; Richard F. Doherty, 61 Lion La., Westbury, N.Y. 11590

[21] Appl. No.: 719,733

[22] Filed: Sep. 2, 1976

[51] Int. Cl.² .............................................. A61M 5/30
[52] U.S. Cl. .................................. 128/173 H; 173/53
[58] Field of Search .......... 128/173 H, 173 R, 218 R, 128/218 A, 218 C, 218 F; 185/37, 39; 173/53, 56, 54

[56] References Cited

U.S. PATENT DOCUMENTS

| | | | |
|---|---|---|---|
| 2,722,931 | 11/1955 | May | 128/173 H |
| 3,131,692 | 11/1964 | Love | 128/218 R |
| 3,842,295 | 10/1974 | Doherty | 128/173 H |

FOREIGN PATENT DOCUMENTS

| | | | |
|---|---|---|---|
| 724,974 | 2/1955 | United Kingdom | 128/173 H |

*Primary Examiner*—Robert W. Michell
*Assistant Examiner*—Henry J. Recla
*Attorney, Agent, or Firm*—Amster & Rothstein

[57] ABSTRACT

The within improved innoculator is of the type that causes the injection of medication without a skin-penetrating needle, relying instead on a skin-penetrating jet produced by the force of a released compression spring, wherein the improvement resides in a mechanical device for effectively loading the spring of the innoculator.

5 Claims, 4 Drawing Figures

DEVICE FOR SPRING-LOADING A NEEDLELESS INNOCULATOR

The present invention relates generally to medication-dispensing innoculators which function without an injection needle, such as the innoculator of my prior U.S. Pat. No. 3,815,594, and more particularly to an effective device for mechanically loading or placing the spring which operates the innoculator under compression preparatory to innoculating service thereof.

In its basic construction and mode of operation, except as hereinafter noted, the within needleless innoculator is similar to that of my prior patented innoculator of U.S. Pat. No. 3,815,594, which patent is incorporated by reference herein. Both innoculators, as generally understood, by avoiding the use of a skin-penetrating injection needle correspondingly avoid pain and anxiety for the patient. For these innoculators, and those designed by others, the medication is dispensed in a jet stream of sufficient force, produced by a released compression spring, to penetrate the patient's skin with significantly diminished pain and physical awareness by the patient.

With a needleless innoculator, the jet-producing spring thereof must be compressed or loaded prior to each use, a requirement which heretofore has not been solved in a totally satisfactory manner. My previously patented innoculator, noted above, uses the magnetic field of a solenoid coil to produce the necessary relative movement of the innoculator components to latch the propelling spring in its compressed state, after which the innoculator is then readily removed from within the demagnetized solenoid coil. Although my patented innoculator avoids any complicated mechanisms requiring coupling to, and uncoupling from, the device which loads the spring, since all that is necessary is to insert the innoculator within and remove it from the solenoid coil, it is necessary to have this electrical component and thus, of course, access to electricity. There is no known device for loading the spring of a needleless innoculator mechanically, i.e. without an electrically powered device, that is effective and avoids complicated coupling mechanisms. This is undoubtedly because the gripping engagement of the depending end of the slidable inner core of the innoculator must be firm to cause compressing movement thereof against the resistance of the propelling spring, and such firmness in this gripping engagement of necessity must involve clamps and a clamping function.

Broadly, it is an object of the present invention to provide an improved needleless innoculator overcoming the foregoing and other shortcomings of the prior art. Specifically, it is an object to provide a mechanical device into which, and from which, the innoculator is readily movable, but which operates to effectively cause loading or compression of the innoculator spring preparatory to medication-dispensing service of the innoculator.

As already noted, the within needleless innoculator is of the type having an inner core depending from an external housing which is slidable in said housing under the propulsion of a spring incident to dispensing medication. In combination with such an innoculator there is provided a device for mechanically loading the innoculator spring which includes a base on which there is a stationary shaft defining a rotation axis and having circumferentially spaced holding teeth radially extending therefrom. This shaft is mounted in a clearance position on the base and a housing member, including means defining a connector-receiving compartment oriented transversely of and in facing communication with the stationary shaft, is operatively arranged to partake of a pivotal traverse in eccentric relation about the stationary shaft. Additionally, a connector is provided having an operative inserted position within the connector-receiving compartment, said connector having a depending end with lateral means projecting therefrom for establishing meshing engagement with the holding teeth of the stationary shaft during said pivotal traverse thereof. In the opposite end of the connector there is an opening bounding an innoculator-receiving compartment for the inner core depending end. Completing the mechanical device is innoculator gripping means circumferentially spaced about the last named compartment opening movable from a starting position radially inward for establishing gripping contact with the depending inner core, but only after initial angular movement of the connector through said pivotal traverse. Due to this delay in establishing gripping contact, the depending innoculator inner core end is readily inserted and removed from the device in its operative position when, as noted, there is an absence of established gripping contact as occurs prior to and during said initial angular movement, but otherwise the innoculator is held by said established gripping contact for the loading of its propelling spring as occurs during the balance of the angular movement of said pivotal traverse.

Figure 2:
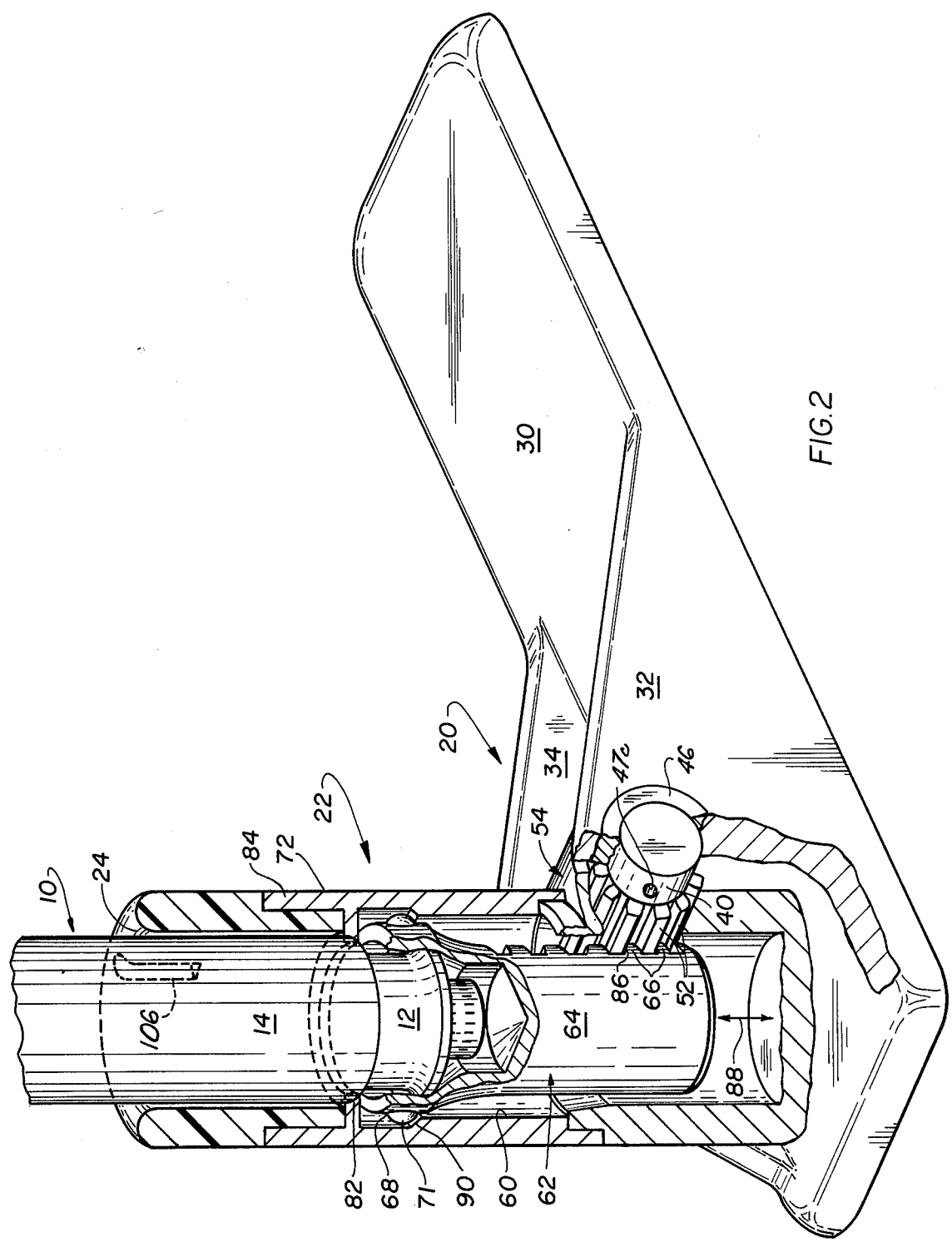
Figure 3:
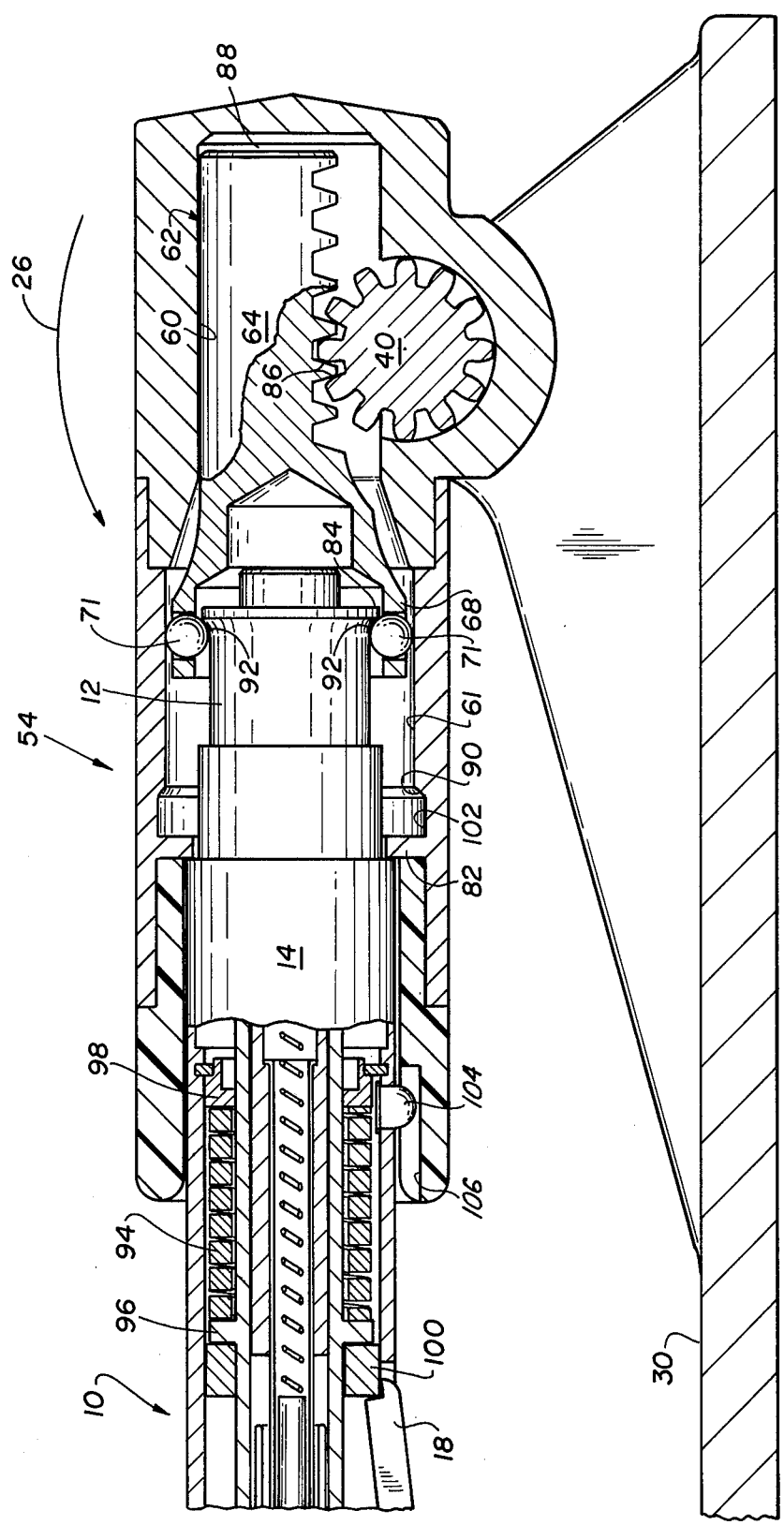
Figure 4:
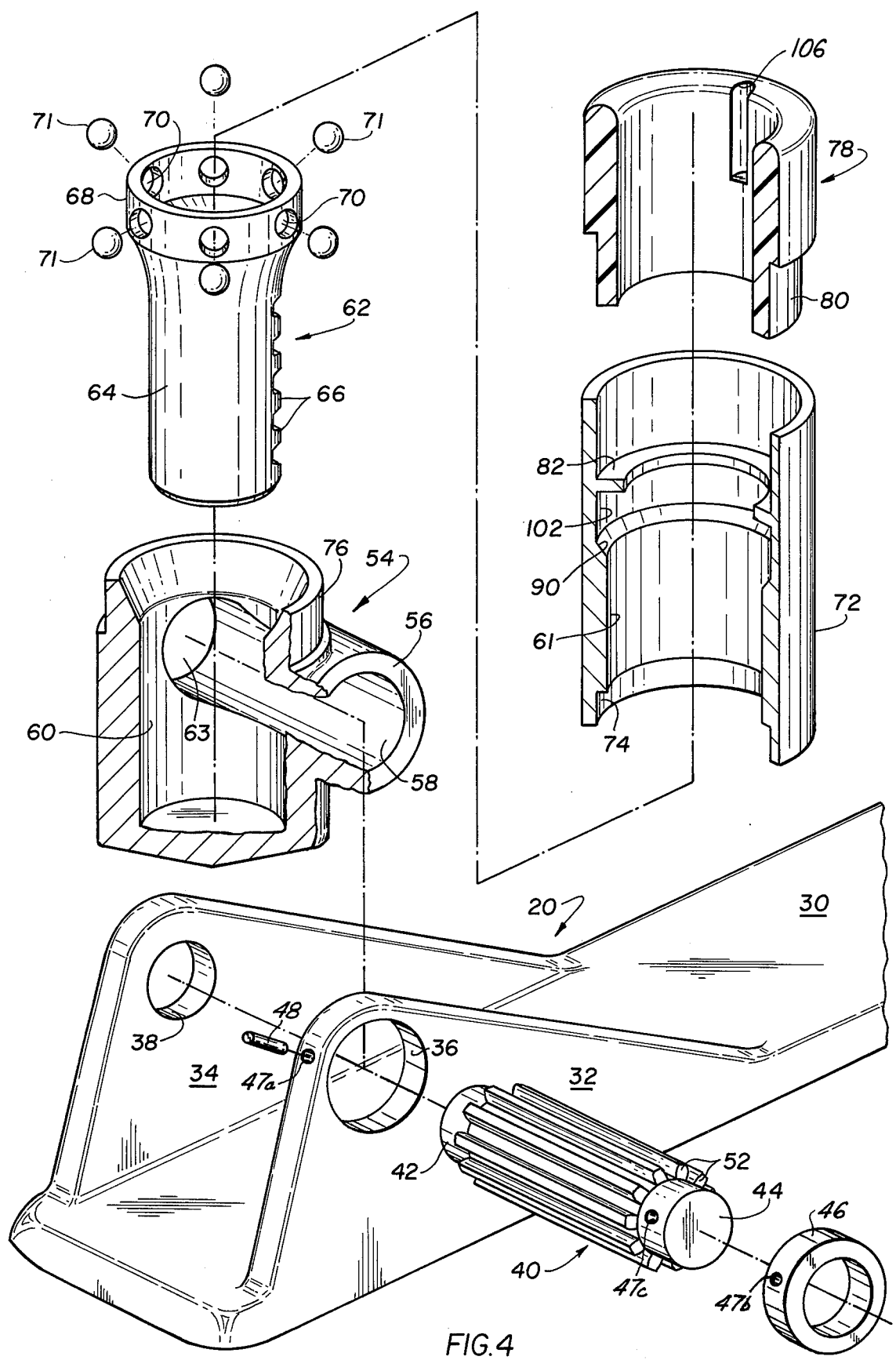

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein:

FIG. 1 is a perspective view of an exemplary spring-powered needleless innoculator and its cooperating inventive device hereof for mechanically loading the spring of this innoculator;

FIGS. 2 and 3 illustrate the sequence in which the spring of the innoculator is compressed or loaded. More particularly, FIG. 2 is a perspective view, with portions partially broken away to illustrate internal structural features, which illustrates the manner in which the depending end of the innoculator is inserted and removed from the spring-loading device, the same being in its starting or ending condition, as the case may be, and thus prior to the establishment of gripping contact with said innoculator depending end as is necessary to produce compression or loading of the innoculator spring;

FIG. 3 is a side elevational view, in longitudinal cross-section, which illustrates how gripping contact is established with the innoculator depending end so as to result in compression of the innoculator spring, the same occurring as a result of a pivotal traverse through approximately 90°, i.e. a traverse from the position illustrated in FIG. 2 to that illustrated in FIG. 3; and FIG. 4 is an exploded view illustrating the various components which comprise the spring-loading device hereof, some of the components being illustrated in longitudinal cross-section so as to better illustrate internal structural features thereof.

Illustrated in FIG. 1 is an exemplary needleless innoculator, generally designated 10, which, for present purposes, may be understood to be constructed and to operate substantially similar to the innoculator illustrated and described in my prior U.S. Pat. No. 3,815,594, which is incorporated by this reference in its entirety herein. As is generally understood, a needleless innoculator utilizes a spring or a spring equivalent, such as belleville washers, to urge an inner core 12 through movement within an external housing 14 so as to cause the dispensing of medication from an exit opening 16 with sufficient force to actually penetrate through a patient's skin and thus enable an injection of medication without actually using a skin-piercing needle. As is further understood, the forces involved require the use of a heavy compression spring, the compression or loading of which in turn presents a formidable problem. In the case of the patented innoculator previously referred to, the loading of the spring thereof is accomplished by fabricating the innoculator depending end 12 of a magnetizable material and disposing the same in a loading device which includes a solenoid coil in surrounding relation to said depending end 12. It is further provided that when the solenoid coil is energized, that this is effective in causing relative movement of the inner core 12 relative to the external housing 14 which results in compression of the propelling spring. The spring is maintained in its compressed state by a latch 18 which, of course, is released subsequently when the innoculator end 16 is in injecting relation to the patient. As an alternative to the electrical means for loading the spring of the innoculator 10 there is herein proposed a device 20 for mechanically achieving this result. Mechanical device 20 is characterized by being more simply constructed and operated, is less expensive, and of course does not require electricity for its operation, as well as providing other noteworthy advantages and benefits.

Still referring to FIG. 1, the spring-loading device 20 of the present invention includes an assembly of components, generally designated 22, having an upper cylindrical opening 24 in which the depending innoculator end 12 is inserted, and after which the two are simultaneously urged through a pivotal traverse 26 which loads or compresses the spring of the innoculator. Next, the assembly is returned in a reverse pivotal direction to the starting position illustrated in FIG. 1, in which the innoculator is then readily withdrawn from the opening 24. Thus, in accordance with this very simple procedure, the innoculator 10 is prepared for medication-dispensing service.

Before explaining in detail how the operation of the device 20, and more particularly the pivotal traverse 26 of assembly 22 thereof achieves loading of the innoculator spring, it should first be noted that it is significant that the innoculator depending end 12 is readily inserted and removed from the opening 24 in the FIG. 1 position of device 20. That is although firm gripping contact is ultimately made with the depending end 12 so that there can be relative movement between the inner core and the external housing 14 so as to load the spring which is operatively disposed therebetween, in the upright or starting and ending condition of assembly 22, there is a significant lack of gripping contact established with the innoculator depending end 12 so that it can be readily inserted and removed. Stated another way, the gripping contact which results in the loading of the spring is established only after initial angular movement 28, and remains for the balance of the pivotal traverse 26 when it is required for purposes of loading the innoculator spring. In this simple and effective way, therefore, the device 20 avoids any need for complicated structure for firmly engaging, and then effectuating disengaging from, the innoculator depending end 12, even though such engagement exists during the loading of the spring thereof.

Reference is now made to FIGS. 2, 3 and 4 which illustrate structural details of the device 20. Molded as an integral part of an anti-tipping plate 30 are two spaced walls 32 and 34 which are formed or provided with cylindrical openings 36, 38 respectively. A stationary shaft 40 with laterally extending hubs or trunions 42 and 44 is mounted to extend in spanning relation between the walls 32 and 34, the hub 42 being inserted in the opening 38 and the opposite hub 44 in the opening 36. Completing the shaft 40 are a series of circumferentially spaced radially extending teeth, individually and collectively designated 52, the function of which will soon be described.

Opening 36 is sized to receive the shaft with teeth 52. After insertion of member 40 a sleeve bushing 46 is inserted between hub 44 and opening 36. To hold the shaft 40 against rotation and thus to maintain it stationary and also to secure bushing 46, use is made of a locking pin 48, which is inserted in bores 47a, 47b and 47c. As shown in FIG. 1, a decorative cover 51 may be affixed by any conventional means to cover the shaft end.

The remainder of device 20, or what was previously identified as assembly 22, actually consists, in a preferred embodiment, of four units. One unit is a pivotally traversable housing, generally designated 54, which has a curved wall 56 which bounds an internal cylindrical opening 58 which in the assembled condition of the unit 20 accommodates the shaft 40 and permits the housing 54 to be pivotally traversable about the shaft 40. In this connection, member 54 also includes a transversely oriented cylindrical opening 60 which intersects the cylindrical opening 58 and, at said intersection, such as at 63, there is an opening in facing communication with the opening 58. Thus, that which is disposed in the opening 60, as will soon be described, can and does effectively make physical contact with the stationary shaft 40 which is operatively disposed in the horizontally oriented opening 58, this contact being made through the opening 63.

Operatively disposed in the vertically oriented opening 60 is unit 62 which actually forms the connection, during the loading of the innoculator spring, between the innoculator and the loading device 20. Connector 62 includes a depending cylindrical portion 64 which has rack and pinion-type teeth, individually and collectively designated 66. In the assembled condition of the connector 62 within the housing 54, teeth 66 establish meshing engagement with teeth 52 of the stationary shaft 40, all as will be subsequently explained in detail. Completing the construction of connector 62 is an integral annular upper portion 68 with circumferentially spaced openings 70 which each has cooperating ball bearing or ball means 71 positioned therein. More particularly, as will be explained in detail subsequently, each ball 71 is confined generally within a cone-shaped opening 70, which is tapered inwardly toward the center of annular member 68 and, more specifically, is moved from a starting position outwardly of annular member 68 into a radially inward position, the latter position enabling it to establish gripping contact with the innoculator depending end 12 preparatory to loading the spring thereof.

The remaining units of assembly 22 are cylindrical units, generally designated 72 and 78, which are assembled to each other and then assembled to the housing unit 54 by force fitting the counterbore opening 74 of cylinder 72 about the upstanding grip 76 of housing 54. Unit 78, also generally cylindrical in shape like cylinder 72, but preferably fabricated of plastic, is force fit or otherwise attached to the cylinder 72 by inserting the depending cylindrical portion 80 thereof within the upper counterbore 82.

The operation of the device 20 will now be explained with particular reference to the FIGS. 2 and 3. In the starting position illustrated in FIG. 2, the assembled components 22 have the generally vertically oriented attitude as illustrated. Innoculator 10 is inserted within opening 24, with the result that the external housing 14 which surrounds the inner core 12 abuts against the radially extending lip 82 of the cylindrical extension 72 of the pivotally traversable housing 54. Also strategically located at this time below the ball gripping means 71 which are disposed within openings in the upper annular portion 68 of the connector 62 is a laterally extending lip 84 on the depending end of the inner core 12. It should be noted that the diameter for the lip 84 and for the annular portion 68 are selected to allow easy passage of the core 12 into and out of the upper portion of the connector 62 when the balls 71 are radially outwardly disposed as illustrated in FIG. 2.

Still referring to FIG. 2, it should be noted that at least one tooth 66 of the connector 62 is in meshing engagement, as at 86, with a cooperating radially extending tooth 52 of the stationary shaft 40. Because of this meshing engagement which is maintained between the teeth 66 and 52, but not necessarily the same teeth, the meshing engagement being progressively advanced about the shaft 40 as the housing 54 is urged through its pivotal traverse 26, it of course must follow that the connector 62, other than partaking of the pivotal traverse is not moved axially along the opening 60. That is, since shaft 40 is stationary, then obviously connector 62 because of meshing engagement established at point 86 cannot move beyond this point of established contact. Thus, connector 62 cannot advance along the cylindrical opening 60 in the direction of the innoculator 10. However, there is clearance 88 beneath the connector 62 which is ultimately occupied by the cylindrical connector body 64 as housing 54 is urged through its pivotal traverse 26, thereby causing relative movement between the connector 62 and pivotally traversable housing 54. Stated another way, during the pivotal traverse 26, the rotation axis for the connector 62 occurs at the interface 86 of the meshing teeth 52 and 66, whereas the rotation axis for the housing member 54 is the stationary shaft 40, and thus these two rotation axes for these members result in differential movement therebetween.

The result of the foregoing can be better understood by reference to FIG. 3 which illustrates the housing member 54 after its pivotal traverse 26. As indicated in this figure, the depending cylindrical portion 64 of the connector 62 is still in meshing engagement with the stationary shaft 40, although contact 86 therebetween has been advanced in the direction of the pivotal traverse. Differential movement has resulted in the connector 62 occupying practically all of the clearance 88 which originally existed beneath the cylindrical portion 64. More important, the relative position of the connector 62 within the housing 54 is one in which the annular upper portion 68 of the connector 62 is carried well below a conical cam surface 90 appropriately machined about the upper end of the cylindrical opening 61 of the cylindrical extension 72 of housing 54. As a consequence, the gripping balls 71 are cammed radially inward during passing over the conical cam surface 90 and are held in this inward condition during contact with the surface bounding the opening 61 during relative movement between the connector 62 and the housing 54 as occurs during the pivotal traverse 26. As clearly shown in FIG. 3, this radially inward position of the gripping balls 71 defines a smaller diameter than the laterally extending lip 84 of the innoculator inner core 12, and thus there is effective gripping contact established between the connector 62 and the inner core 12 at circumferentially spaced locations, individually and collectively designated 92. Gripping contact established at these multiple locations 92 has been found in practice to be firm enough and adequate to withstand the forces generated during the compression loading of the innoculator spring, designated 94 in FIG. 3, which is operatively disposed or seated between cooperating lateral projections 96 and 98 of the inner core 12 and stationary housing 14, respectively, of the innoculator 10. Once spring 94 is effectively compressed, as generally understood, latch 18 (again referring to FIG. 3), engages the inner core 12 at an annular ring 100 mounted thereabout to maintain the operative axially displaced positions between the innoculator external housing 14 and slidable inner core 12.

Following the latching of the innoculator inner core 12, the pivotal traversable assembly 22, and more particularly the housing 54 thereof, is urged through a reverse direction pivotal traverse about the stationary shaft 40, thus returning it to its starting FIG. 2 position. This, of course, results in relative movement between the connector 62 and housing member 54 which positions the gripping balls 71 above the cam surface 90, thus allowing the balls 71 to move radially outward into the counterbore 102 of the cylindrical extension 72. As already noted, this releases the balls 71 from their gripping contact at the locations 92 with the laterally extending lip 84 of the inner core 12. In the absence of this established gripping contact between the connector 62 and the inner core 12, the innoculator 10 is of course then free to be readily removed from within the opening 24, and it is in its required spring-loaded condition preparatory to being used for medication-dispensing service.

To facilitate handling by the user, pin 104 must engage slot 106. This insures that the user will have the apparatus properly oriented after cocking.

From the foregoing description it should be readily appreciated that device 20 described herein, and particularly the mode of operation thereof which contemplates establishing gripping contact with the inner core 12 of the innoculator 10 only after an initial angular movement of the power or spring-loading traverse 26, provides a significantly effective device for preparing the needleless innocualtor 10 for use. Specifically, the innoculator 10 in its inserted condition within the assembly 22, due to its length, functions somewhat as a lever and has the mechanical advantages thereof, so that it is relatively simple to urge the assembly through the portion of the pivotal traverse 26 which results in the compression loading of the propelling spring. Also, as already noted, in the generally upright or FIG. 2 position of device 20, there is a desired absence of any gripping contact with the depending end 12 of the innoculator so that it is not only readily inserted within the opening 24 prior to loading the spring, but also it is readily removed therefrom after the spring has been loaded.

While the apparatus has been described as embodied in a needleless innoculator, the invention is useful for compressing springs in other spring-actuated devices, such as guns, punches, hammers, etc. The term medication as used in the claim is intended to encompass other liquids whether or not intended for medicinal purposes.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In combination, a needleless innoculator of the type having an elongated external housing including medication dispensing means disposed at one end and an inner core slidably mounted within said housing and depending externally from the other end of said housing, spring means biasing said core towards said one end, means associated between said core and said medication dispensing means for dispensing the medicament subcutaneously, a connector and a device for mechanically loading said spring preparatory to said medication-dispensing service of said innoculator, said device comprising a base, a stationary shaft transversely disposed to the longitudinal axis of said base and defining a rotation axis and having circumferentially spaced holding teeth radially extending therefrom mounted in a clearance position on said base, a housing member defining a connector-receiving compartment including means for slidably receiving and holding said depending core and innoculator housing, said housing member being oriented transversely of and in facing communication with said stationary shaft, said connector-receiving compartment of said housing member being opertively mounted on said shaft in a pivotal traverse eccentric relation about said stationary shaft, said connector having an operative inserted position within said connector-receiving compartment, said connector having a depending end with lateral teeth egaging means projecting therefrom for establishing meshing engagement with said holding teeth of said stationary shaft during said pivotal traverse thereof, the opposite end of said connector including said means for receiving and holding said core defining an opening therein, said inner core depending end being slidably inserted and removable within said opening, and innoculator core gripping means circumferentially spaced about said opening movable from a starting position radially inward for establishing gripping contact with said depending inner core only after initial angular movement of said connector through said pivotal traverse thereof, whereby said depending innoculator inner core end is readily inserted and removed from said device in the absence of established gripping contact therewith during said initial angular movement but otherwise is held by said established gripping contact for the loading of said spring means during the balance of the angular movement of said pivotal traverse.

2. A device for spring-loading a needleless innoculator as defined in claim 1 wherein said depending innoculator inner core includes a lateral lip and said innoculator gripping means includes ball means disposed in openings in the wall structure of said connector and a cooperating camming surface on said housing member adjacent said openings encountered by said ball means whereby, said lateral lip is engaged by said ball means in said radially inward cammed position thereof, and said camming surface of said housing member is arranged to extend for an extent which contributes to said radially inward cammed position of said ball means for an angular extent coextensive with all but an initial angle of said pivotal traverse only after said initial angular movement of said pivotal traverse which causes relative movement between said connector and said housing member.

3. A device for spring-loading a needleless innoculator as defined in claim 2 wherein said innoculator external housing extends in surrounding relation about said inner core thereof, and said housing member includes an annular upper surface against which said external housing is in pushing contact during said pivotal traverse while said inner core is held against such pushing movement by said established contact thereof with said connector in turn in meshing engagement with said stationary shaft holding teeth.

4. A device for spring-loading a needleless innoculators as defined in claim 3 wherein said base includes spaced apart walls, said stationary shaft being mounted in spanning relation between said walls, and said housing member being pivotally traversable about said stationary shaft in the clearance between said walls.

5. The combination of claim 1 wherein said innoculator serves as a handle for moving said housing member.

* * * * *